(12) United States Patent
Ahadian et al.

(10) Patent No.: US 8,854,609 B2
(45) Date of Patent: Oct. 7, 2014

(54) INTEGRATED OPTICAL TIME DOMAIN REFLECTOMETER

(75) Inventors: Joseph F. Ahadian, San Marcos, CA (US); Charles B. Kuznia, Encinitas, CA (US); Richard T. Hagan, Mission Viejo, CA (US); Ricard J. Pommer, Carlsbad, CA (US)

(73) Assignee: Ultra Communications, Inc., Vista, CA (US)

( * ) Notice: Subject to any disclaimer, the term of this patent is extended or adjusted under 35 U.S.C. 154(b) by 72 days.

(21) Appl. No.: 13/638,794

(22) PCT Filed: Mar. 31, 2011

(86) PCT No.: PCT/US2011/030792
§ 371 (c)(1),
(2), (4) Date: Dec. 11, 2012

(87) PCT Pub. No.: WO2011/123687
PCT Pub. Date: Oct. 6, 2011

(65) Prior Publication Data
US 2013/0208264 A1 Aug. 15, 2013

Related U.S. Application Data

(60) Provisional application No. 61/319,385, filed on Mar. 31, 2010.

(51) Int. Cl.
| | | |
|---|---|---|
| G01N 21/00 | (2006.01) | |
| G01M 11/00 | (2006.01) | |
| G01N 21/55 | (2014.01) | |
| H04B 10/071 | (2013.01) | |
| G01N 21/958 | (2006.01) | |

(52) U.S. Cl.
CPC ......... *G01N 21/958* (2013.01); *G01M 11/3154* (2013.01); *G01N 21/55* (2013.01); *H04B 10/071* (2013.01); *G01M 11/3145* (2013.01)
USPC ...................................... 356/73.1; 356/237.1

(58) Field of Classification Search
CPC .................... G01M 11/3145; G01M 11/3127; G01M 11/3154; G01N 21/55; G01N 21/958
USPC ........................ 356/73.1, 237.1, 239.1, 239.2; 398/9–24
See application file for complete search history.

(56) References Cited

U.S. PATENT DOCUMENTS

| | | |
|---|---|---|
| 5,142,284 A | 8/1992 | Trent |
| 5,777,727 A | 7/1998 | Sato |
| 5,940,196 A | 8/1999 | Piehler |
| 6,910,812 B2 | 6/2005 | Pommer |
| 7,280,189 B2 | 10/2007 | Weller |
| 2008/0094615 A1 | 4/2008 | Harres |
| 2010/0271622 A1* | 10/2010 | Hori .............................. 356/73.1 |

OTHER PUBLICATIONS

International Application No. PCT/US2011/030792, International Search Report and Written Opinion, mailed Jun. 15, 2011 (15 p.).

* cited by examiner

*Primary Examiner* — Tri T Ton
(74) *Attorney, Agent, or Firm* — TechLaw LLP—Epstein

(57) ABSTRACT

An optical time domain reflectometry system is described which provides low-power, low weight, optical fiber system integrity measurements in an in-situ optical fiber system. The system can be integrated within the transmitter component to allow both data transmission and OTDR measurement functions. A method of providing several different modes of OTDR measurement through external control is also disclosed.

24 Claims, 8 Drawing Sheets

INTEGRATED OPTICAL TIME DOMAIN REFLECTOMETER

CROSS REFERENCE TO RELATED APPLICATION(S)

This application is a U.S. National Stage Filing under 35 U.S.C. 371 from International Patent Application Ser. No. PCT/US2011/030792, filed Mar. 31, 2011,and published on Oct. 6, 2011 as WO 2011/123687 A1, which claims the benefit of priority to U.S. Provisional Patent Application No. 61/319,385, titled "Integrated Optical Time Domain Reflectometer," filed Mar. 31, 2010, the contents of each of which are hereby incorporated by reference in their entireties.

BACKGROUND

This invention relates to the field of fiber optics and the detection of faults in fiber optic systems.

SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

One aspect of the present disclosure is a data line sharing, optical time domain reflectometer (OTDR) apparatus for determining a distance of a disruption in a fiber optic line, comprising: a multiplexer having a coupled input for a data signal from an external source and a coupled input for an OTDR signal; OTDR circuitry generating the OTDR signal; a processor controlling the OTDR circuitry; a light transmitter system coupled to an output of the multiplexer; a light detector coupled to the OTDR circuitry; and a bi-directional optical coupling structure in a light path of the light transmitter system adapted for channeling a light to an input of the fiber optic line, and for channeling reflected light from the fiber optic line to the light detector; wherein at the generated OTDR signal is at least one of a pulse mode and a step mode is forwarded from the multiplexer to the light transmitter system and input into the bi-directional optical coupling structure and into the fiber optic line, wherein a time delay in the reflected light is used to determine the distance of the disruption in the fiber optic line.

Additional aspects include the features described above, with a partially reflecting surface between the bi-directional optical coupling structure and the fiber optic, line; and/or a mirror to direct the reflected light to the light detector; and/or a transparent substrate coupled on one side to the light transmitter system and light detector, and coupled on an opposite side to the bi-directional optical coupling structure; and/or wherein the bi-directional optical coupling structure has at least one of a light splitting surface and a lens; and/or an input clock signal and input start signal to the ODTR circuitry, to initiate an OTDR measurement sequence; and/or a transimpedance amplifier coupled to an output of the light detector; and/or a track and hold circuit coupled to an output of the transimpedance amplifier; and/or wherein an output of the ODTR circuitry is input into the track and hold circuitry; and/or a differential variable gain amplifier coupled to an output of the track and hold circuitry; and/or the light transmitting system includes a vertical cavity surface emitting laser.

In another aspect of the present disclosure, a method for performing optical time domain reflectometry with a data line in a signal path to a fiber optic line is provided, comprising: generating an OTDR signal from OTDR circuitry coupled to a multiplexer with a data signal input also coupled to the multiplexer, operating the OTDR signal in at least one of a pulse mode and step mode; driving a light transmitter system that is coupled to an output of the multiplexer based on the OTDR signal; forwarding light from the light transmitter system to the fiber optic line via a bi-directional optical coupling structure; channeling reflected light from the fiber optic line via the bi-directional optical coupling structure to a light detector; measuring the reflected light time delay as compared to a start time of the OTDR signal; averaging measured delays to obtain an average; and calculating a distance of a disruption in the fiber optic line based on the obtained average.

Additional aspects include the features described above wherein the pulse mode is operated in at least one of a normal mode and difference mode; and/or further sending at least two reference signals from the ODTR circuitry to a track and hold device; and/or further applying a differential variable gain to an output of the track and hold device; and digitizing an output of the differential variable gain, wherein the calculated distance is determined by a processor operating on information from the digitized output; and/or further generating an OTDR distance map; and/or further sending a start signal to the ODTR circuitry; triggering ODTR measurement based on determined triggering delays; waiting for ODTR measurement completion; triggering an analog-to-digital conversion of measured information; accumulating an average of the measured information; and storing the average as the obtained average; and/or further obtaining a secondary obtained average based on a plurality of sets of determined triggering delays; and calculating the distance of a disruption in the fiber optic line based on the obtained average being derived from the plurality of sets of determined triggering delays; and/or wherein the plurality of sets of determined triggering delays is based on a completion of sweep determination.

In another aspect of the present disclosure, a data line sharing, optical time domain reflectometer (OTDR) apparatus for determining locations of a disruptions in a fiber optic line, is provided, comprising: means for multiplexing a coupled input for a data signal from an external source and a coupled input for an OTDR signal; means for generating the OTDR signal; means for controlling the means for generating; means for generating light, coupled to an output of the means for multiplexing; means for detecting light coupled to the means for generating; and means for bi-directionally coupling light from the means for generating light to an input of the fiber optic line, and for channeling reflected light from the fiber optic line to the means for detecting light, wherein the generated OTDR signal is at least one of a pulse mode and step mode and wherein a time delay in the reflected light is used to determine a distance of the disruption in the fiber optic line.

DETAILED DESCRIPTION

Figure 1:
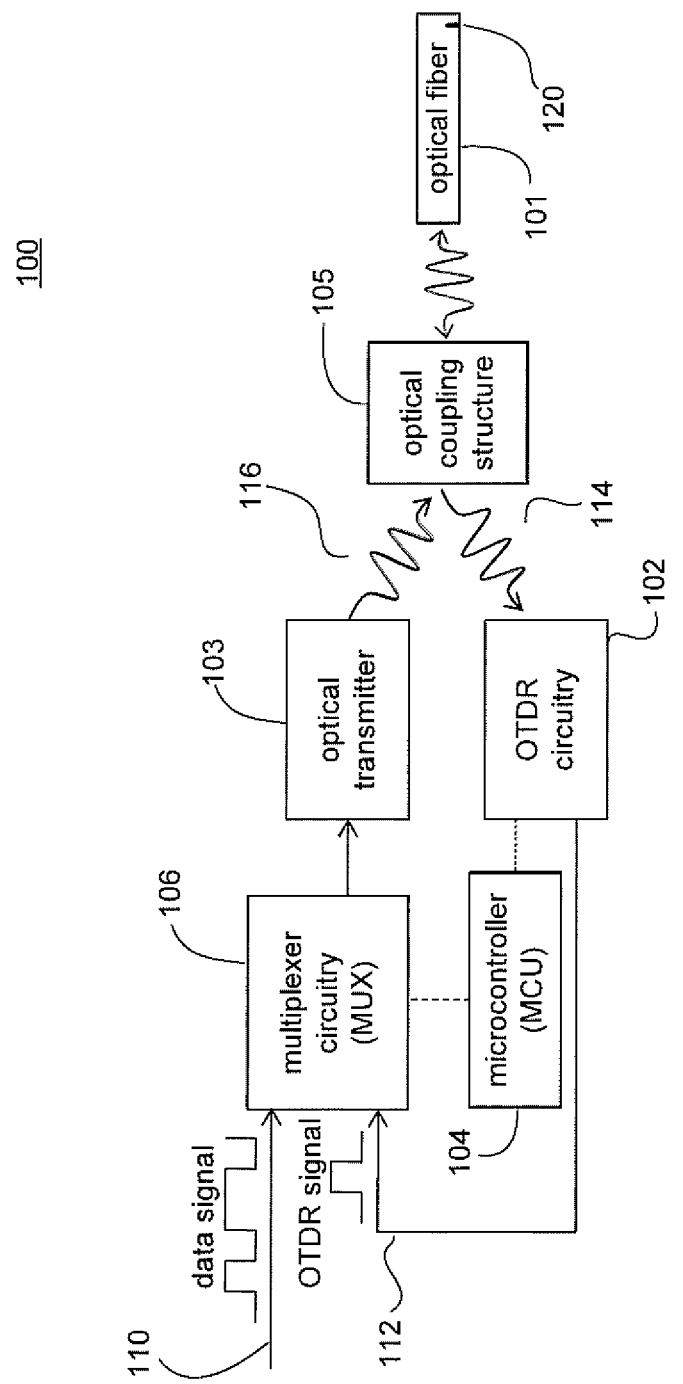
FIG. 1 is block diagram of an exemplary OTDR system integrated with a transmitter.

This application incorporates by reference the subject matter of U.S. Pat. No. 7,095,493 to Harres, titled "Optical Time Domain Reflectometer and Method of Using the Same" and U.S. Pat. No. 5,202,745 to Sarin et al., titled "Polarization Independent Optical Coherence-Domain Reflectometry."

Fiber optics offers high data rate, low weight and electromagnetic interference immunity for data communications, making it suitable for use in modern aircraft and missiles. These platforms require sensor and control data to be distributed throughout the system. If a connector becomes faulty or a fiber is damaged, communication is compromised and action must be taken to accommodate the fault, either repair or re-routing.

One method used to locate faults in a fiber optic system is via optical time domain reflectometry (OTDR). OTDR has been used for many years to diagnose problems in optical fiber systems such as bad connectors, fiber breaks, and even nicks in fibers. OTDR makes use of the fact that once light is transmitted into a fiber, each discontinuity or disruption in a fiber optic system reflects light back toward the light source. By measuring reflected power as a function of time, distances to discontinuities in the fiber optic system can be mapped.

Light travels in glass fibers at approximately 20 centimeters per nanosecond. By measuring the time that it takes light to travel down a fiber, reflect, and travel back again to the light source, the distance to the reflection point can be calculated. A time measurement resolution of 0.1 ns would therefore be able to locate a break to a resolution of about 1 cm.

Currently, OTDR equipment is provided as a stand-alone box containing multiple discrete components to achieve OTDR functionality and a user display. OTDR is performed by disconnecting a fiber from the network and connecting the fiber to a specialized OTDR piece of equipment, which is large, cumbersome and expensive. This requires a skilled technician to travel to the fiber site and gain access to the fibers to perform the measurements. Since this is an expensive and time-consuming task, the OTDR measurement is typically only employed once a fiber optic system had stopped functioning.

Another application for OTDR is in Fiber to the Home (FTTH). In this application, the fiber path from a central office may be split into multiple paths to individual homes. If OTDR is implemented at the individual homes, it would provide a method of isolating fiber faults along the multiple fiber paths. For this large scale implementation, the cost of the OTDR would need to be low.

OTDR systems can create a 'map' of the reflections along the fiber path. Some elements along the fiber create reflections, such as fiber connectors and the optical receiver at the far end of the fiber. Often, the current reflection map is desired to be compared to that of the fiber optic system when it was in a known good state, sometimes called a "baseline" map. Changes to the fiber optic system, such as minor repairs, connect/disconnects, and ageing over time can change the fingerprint. If significant changes have taken place since the "baseline" fingerprint was taken, that makes it more difficult to determine the location of a defect. Therefore, it is desired to monitor the reflection map over time to update the "baseline" fingerprint. Also, minor damage to a fiber optic cable may indicate a reliability concern even if data transmission has not been compromised. Therefore, verification of the system on a regular basis can improve overall reliability of the system by finding problems before they compromise communications.

The present disclosure is an OTDR system realized within a small set of circuits that can be integrated within the active optical modules connected to the fiber network (such as optical transmitters, transceivers, diplexers and triplexers). This integrated OTDR uses low power, has very little weight, and can be implemented inexpensively. Since it can be embedded within the network, it is always available for a testing an optical system.

The circuit, system, and method described herein allow a small, light-weight, low-power OTDR system into an optical transmitter and be present on an optical fiber communication system at all times. The OTDR system can be switched between normal transmitter communications and the OTDR measurement mode through remote software control, for example. In some cases, such as in multi-wavelength systems, the ODTR measurements can be performed without disrupting normal transmitter communications. A microcontroller can interface to the OTDR circuits to allow for flexibility in configuring and controlling measurements. It also can collect and process OTDR data, and communicate data and results externally.

The described OTDR system can be used in various modes. It can be used in a quick go/no-go test for frequent checking of the system. Or it can be used in several diagnostic modes that can measure and store an OTDR map at user-selectable precision and using any of several different methods of acquiring the data. The OTDR can be programmed to operate over variable length fiber systems, for short lengths such as those found in chip-to-chip, or board-level/box-level interconnects (less than 1 meter) and for long lengths found in FTTH applications (greater than 10 km).

The ODTR system described can be integrated within the light emitting component within a fiber network. The light emitting component is responsible for generating light signals utilized in transporting information over a fiber optic cable or optical waveguide. This system can be implemented within single channel, parallel optic transmitters or multiple wavelength transmitters or transceivers. This includes fiber optic transceivers designed for aerospace applications, having a strict overall package height of less than 5 mm. For operation of the OTDR, the transmitter must be outfitted with a method of detecting back-reflected light from the fiber. These and other aspects are detailed in the following Figures.

FIG. 1 is a block diagram of an exemplary optical fiber system 100 containing multiplexer circuitry (MUX) 106, optical transmitter 103, OTDR circuitry 102, processor or microcontroller (MCU) 104, the optical fiber 101, and an optical coupling structure 105. The microcontroller 104 controls whether the system is in communications transmitter mode or OTDR mode. It also controls which type of OTDR measurement to perform and is used to collect the OTDR measurement results. These results can be stored in memory (not shown) or otherwise communicated to the outside world via a communications link (not shown). For normal transmitter communications, the transmitter 103 is in transmit mode. In this mode, the data signal 110 passes through the multiplexer 106 and is converted to a light signal 116 by the transmitter 103. The optical coupling structure 105 couples the light signal 116 into the fiber 101.

In OTDR measurement mode, the microcontroller 104 sets the multiplexer 106 to pass the OTDR signal 112 to the optical transmitter 103. The optical transmitter 103 generates a light signal 116 that is coupled into the fiber 101 by the optical coupling structure 105. Note: some of the light signal 116 may not couple into the optical fiber 101 and may reflect back a light signal 114 into the OTDR circuitry 102. When light that is coupled into and travels down the optical fiber 101 encounters an optical discontinuity or disruption 120, some of the light is reflected back out of the fiber 101, striking the optical coupling structure 105. The optical coupling structure 105 directs some of the back reflected light signal to the OTDR circuitry 102.

By measuring the time between the emitted light signal and the received light signal in the OTDR circuitry 102, the distance to a discontinuity (disruption) 120 can be calculated as d=v*t/2 where d is distance from the transmitter 103, v is the propagation velocity of light in the optical fiber 101, and t is the time difference between light initiation and detection of reflected light. Because the light must travel down the fiber 101 and back, the distance to the discontinuity 120 is half the total distance the light traveled.

Figure 2:
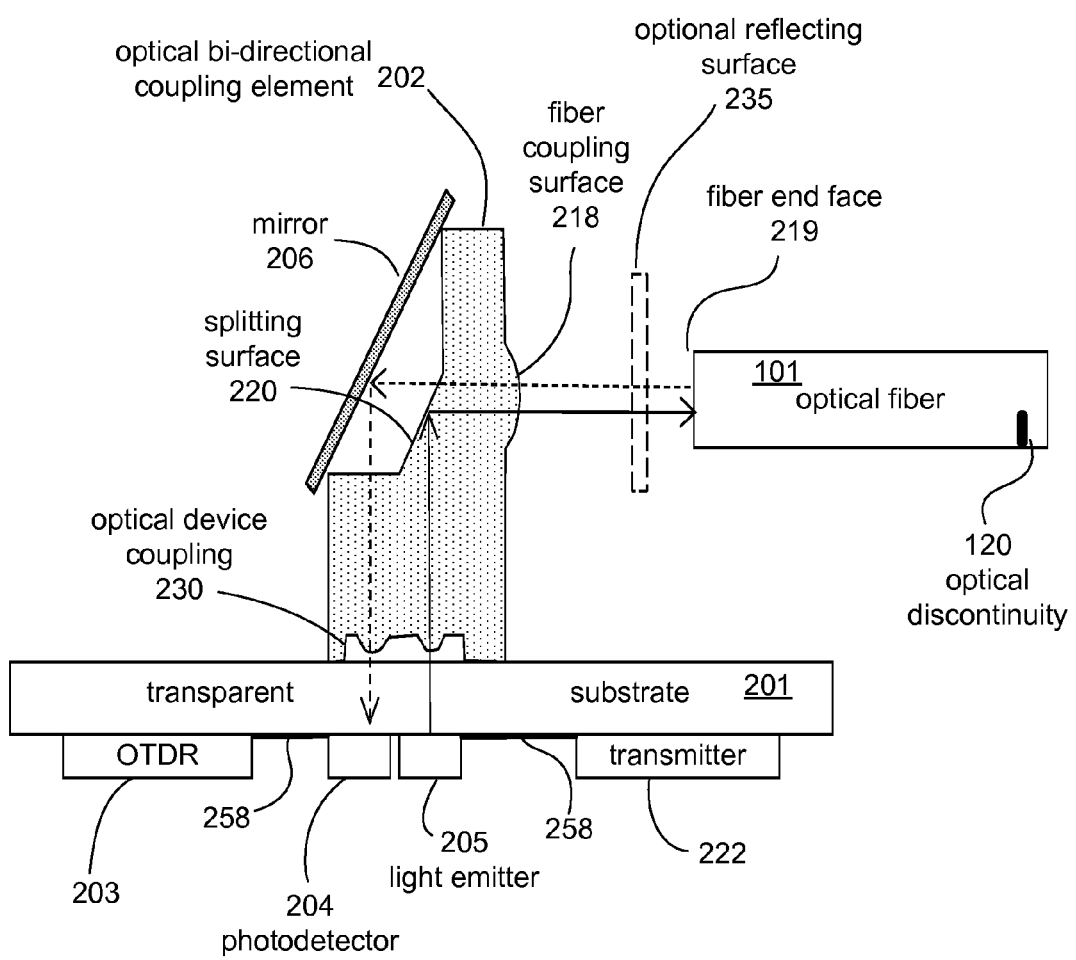
FIG. 2 is a block diagram illustrating an exemplary optical structure and arrangement of electrical components on a transparent substrate.

FIG. 2 is an illustration of an exemplary optical coupling structure and circuit configuration 200. A light emitting device 205 such as, a non-limiting example being a vertical cavity surface emitting laser (VCSEL), is mounted on the bottom surface of transparent substrate 201. It produces light for communications in transmit mode and light for measurements in OTDR measurement mode. The light leaving the emitter 205, represented by the solid line, travels up to the optical coupling element 202 and reflects into the optical fiber 101. Some of the transmitted light may be reflected by the fiber coupling surface 218 or by an optional partially reflecting mirror 235. That reflected light, represented by the light dotted line, hits mirror 206 and then hits a photodetector 204, which, in this example, is mounted on the under surface of the transparent substrate 201. This reflected transmitted light can be used to monitor the average optical power of the light emitter 205 during normal transmitter operation.

When the exemplary system 200 is placed in the OTDR mode, light transmitted by the light emitter 205 is transmitted to the optical fiber 101 and back reflections are coupled into the photodetector 204 as detailed above. Light reflecting from an optical discontinuity or disruption 120 in the optical fiber 101, represented by the dashed line, passes through the partially reflecting optional mirror 235 and back through to mirror 206, then to the photodetector 204. The optical coupling element 202 can have features to increase coupling efficiency, such as lenses, on the fiber coupling surface 218 and on the optical device coupling surface 230. These surfaces 218, 230 and other objects in the light path having reflection characteristics in themselves can offer fixed point/distance landmarks which can be used for calibration purposes, as later described below.

It can be appreciated by one skilled in the art of photonics that various optical structures can be used to create optical coupling with a similar functionality. Therefore, various arrangements, replacements, modifications of the described integrated circuits and discrete circuits may be devised without departing from the spirit and scope of the embodiments shown in FIGS. 1-2.

In the arrangement(s) of FIG. 2, the light emitting device 205 and photodetector device 204 are mounted on the transparent substrate 201 that is formed with electrical conduits 258. The transmitter circuitry 222 and OTDR circuitry 203 can also be mounted on the transparent substrate 201. The conduits 258 provide electrical communication between devices and circuitry mounted on the transparent substrate 201. Mounting these devices and circuitry onto a transparent substrate 201 has advantages for high bandwidth data transport, as the electrical conduits 258 may be shorter and, therefore, offer less signal loss. Alternative packaging schemes may not utilize the transparent substrate 102, rather mounting these devices and circuitry in a variety of other methods that provide the electrical connectivity between devices and optical coupling to the light emitter 205 and photodetector 204.

Figure 3:
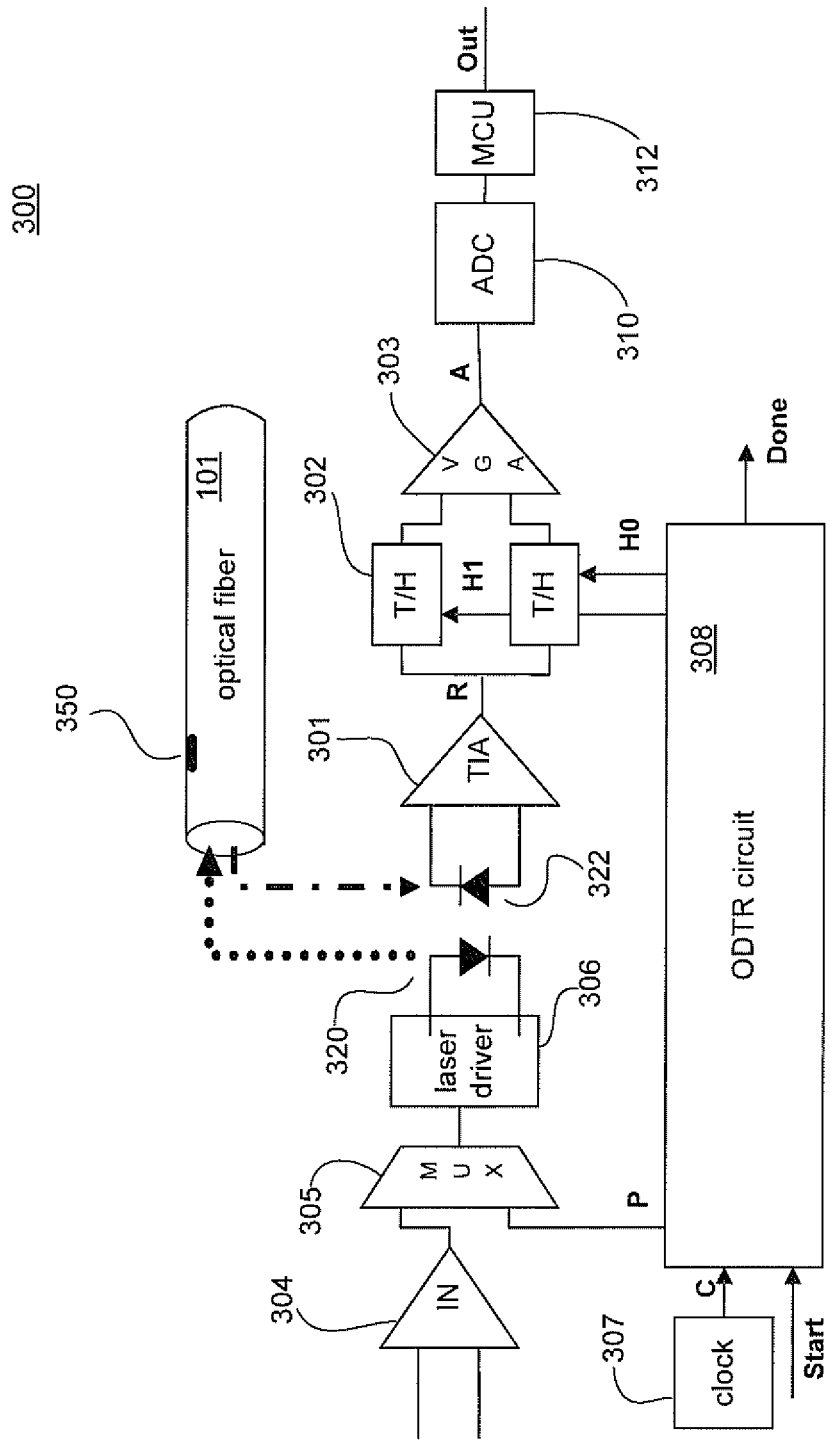
FIG. 3 is a block diagram of an exemplary OTDR system.

FIG. 3 is a circuit block diagram of an exemplary OTDR system. In transmit mode, the processor or microcontroller 312 sets the MUX 305 to a state that passes a signal from the input amplifier 304 to the laser driver 306. In OTDR mode, the microcontroller 312 sets the MUX 305 to pass the signal P from the OTDR circuitry 308 to the laser driver 306.

The OTDR system can be configured by setting desired values for delays of signals H0 and H1. A clock 307 with clock signal C is supplied to set the timing of the OTDR operation. The measurement can be started when a Start signal (for example, from an external source) is received by the OTDR timing generation circuit 308. The signal P from the OTDR timing circuitry 308 passes through the MUX 305 to the laser driver 306 which drives a laser (for, example, a VCSEL) or photoemitter 320, to generate light into the fiber 101. Light travels down the optical fiber 101 and after reflecting off a discontinuity or disruption 350 in the fiber, some light returns and illuminates the photodiode 322 attached to an amplifying device (shown here, using the example of a transimpedance amplifier (TIA)) 301. The amplifier or TIA 301 outputs a voltage proportional to the light intensity striking the photodiode 322 to the track and hold (T/H) circuits 302, one of which holds the signal at a time determined by the H0 signal and the other holds the signal at time determined by the H1 signal. The held signals are fed into another amplifier (shown here, using the example of a differential variable gain amplifier (VGA)) 303. The amplifier or VGA 303 amplifies the difference between the two inputs and this signal is fed into an analog-to-digital converter (ADC) 310 as signal A. The ADC 310 can be incorporated within a processor or MCU 312. The microcontroller 312 then typically further processes and possibly stores the value for later retrieval, depending on the OTDR sampling mode. The same measurement can be repeated many times at the same settings for H0 and H1, so averaging of the signal can be used to increase the signal to noise ratio. The noise drops as the square root of the number of samples, so if 100 measurements are averaged, the noise is reduced by 10×.

The values of H0 and H1 define a location within the fiber 101 in which light reflection is being measured. To make measurements of multiple points along the fiber 101, the values of H0 and H1 are adjusted. It is often desirable to make measurements along the entire length of the fiber 101. In this case, measurements are performed on multiple segments that span the length of the fiber 101. It should be noted that the H0 and H1 times may be changed/combined into a single signal, according to design preference. Therefore, in some designs (for example, a single H0 or single H1 signal), instead of using multiple amplifiers 301, a single amplifier 301 may be devised. Obviously, in some designs, more than two (2) amplifiers 301 may be utilized, according to design preference.

Figure 4A:
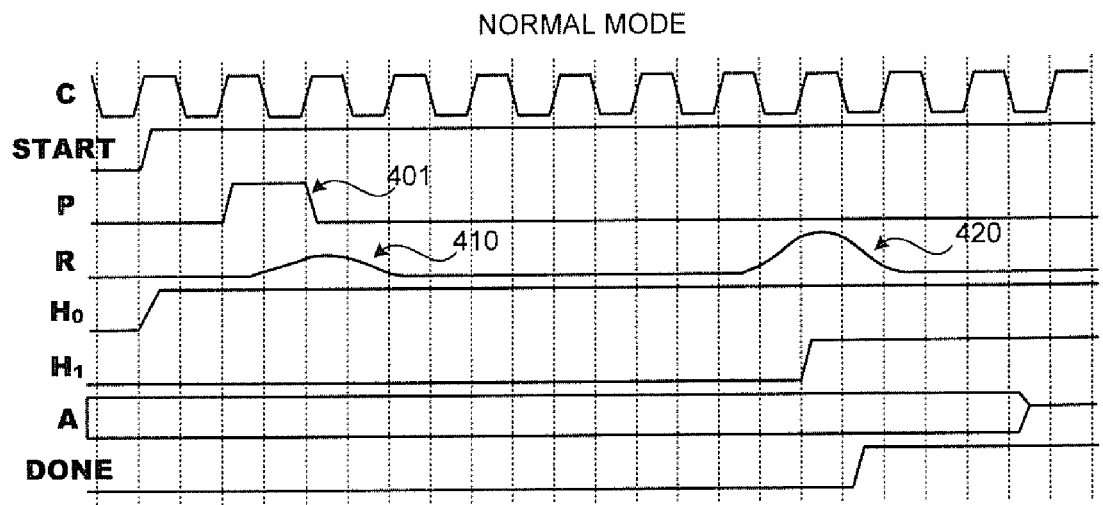
FIG. 4a and FIG. 4b are timing diagrams illustrating normal mode and difference mode OTDR measurement signals.
Figure 4B:
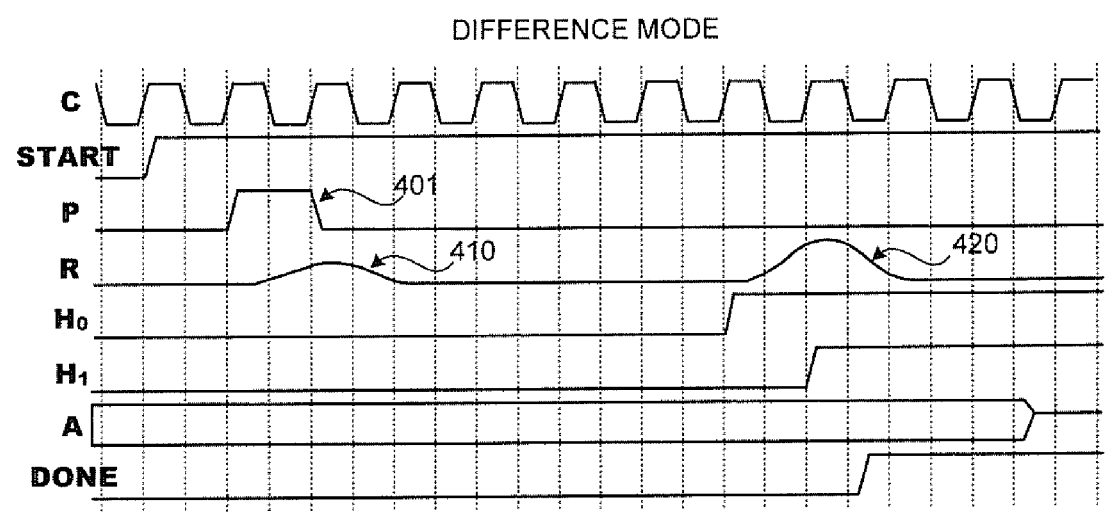

FIGS. 4a and 4b show timing diagrams of two possible OTDR measurement methods. The clock signal C is shown as a continuous sequence and the START signal begins the measurement in both FIGS. In FIG. 4a, what is referred to here as a "normal" OTDR mode operation is shown, where the signal H0 is triggered at the START signal, making a measurement of the output of TIA 301 under conditions of no light being emitted. This "normal" mode can be used to perform a measurement of the noise in the system, which could be from dark current on the photodetector 322, stray light on the photodetector 322, amplifier noise or other potential sources, as examples. This measurement provides a reference level or calibration level for the OTDR measurements. At a later point in time, H1 is triggered to make a second measurement. The difference between the two outputs from the track and hold circuits 302 is then amplified by the VGA 303 to produce the signal A. FIG. 4a also shows the relative timing of the signal P, which generates a pulsed light signal 401 on the light emitter 320, and the signal R resulting from reflected light entering the photodetector 322. Typically, there is a reflection signal 410 shortly after the pulsed light signal 401 from signal P due to reflections from the optics within the transmitter package that are utilized for coupling into the fiber 101. For example, this reflection 410 could be from the fiber coupling surface 218, the optional partially reflecting mirror 235, and/or the fiber end-face 219 as shown in FIG. 2. Since these surfaces are in close proximity of the light emitter 320, a signal R will appear shortly after the pulsed light signal 401. These reflection(s) 410 can be used for calibration purposes, if so desired, as their location (distance) is well known in the test setup. Other surfaces or coupling areas within the transmission path can be utilized for calibration, depending on the configuration. It should be appreciated that in some embodiments, the signal P may consist of several (pulsed) light signals 401 and also may not be of a pulsed form (for example, step, Gaussian, etc.). Accordingly, it is contemplated that a higher resolution can be obtained by having a train of pulses (or other shaped signals) as the signal P.

The second reflection signal 420 on R is due to a discontinuity or disruption in the fiber 101 that creates a reflection at some distance from the emitter 320. This signal will appear at a time corresponding to the time-of-flight required for the emitted pulse to travel to the discontinuity and back to the photodetector 322. By adjusting the H1 signal until it coincides with the light returning from the discontinuity, the physical location of the discontinuity can be determined. The amplitude of the signal A also indicates the magnitude of the reflection.

FIG. 4b shows what is called here a difference-mode measurement. In this case, H0 is triggered shortly before the reflected pulse 420 is received and H1 is triggered shortly thereafter. The short delay between H0 and H1 reduces the effect of signal drift over time, which may improve signal to noise ratio in certain circumstances.

Figure 5:
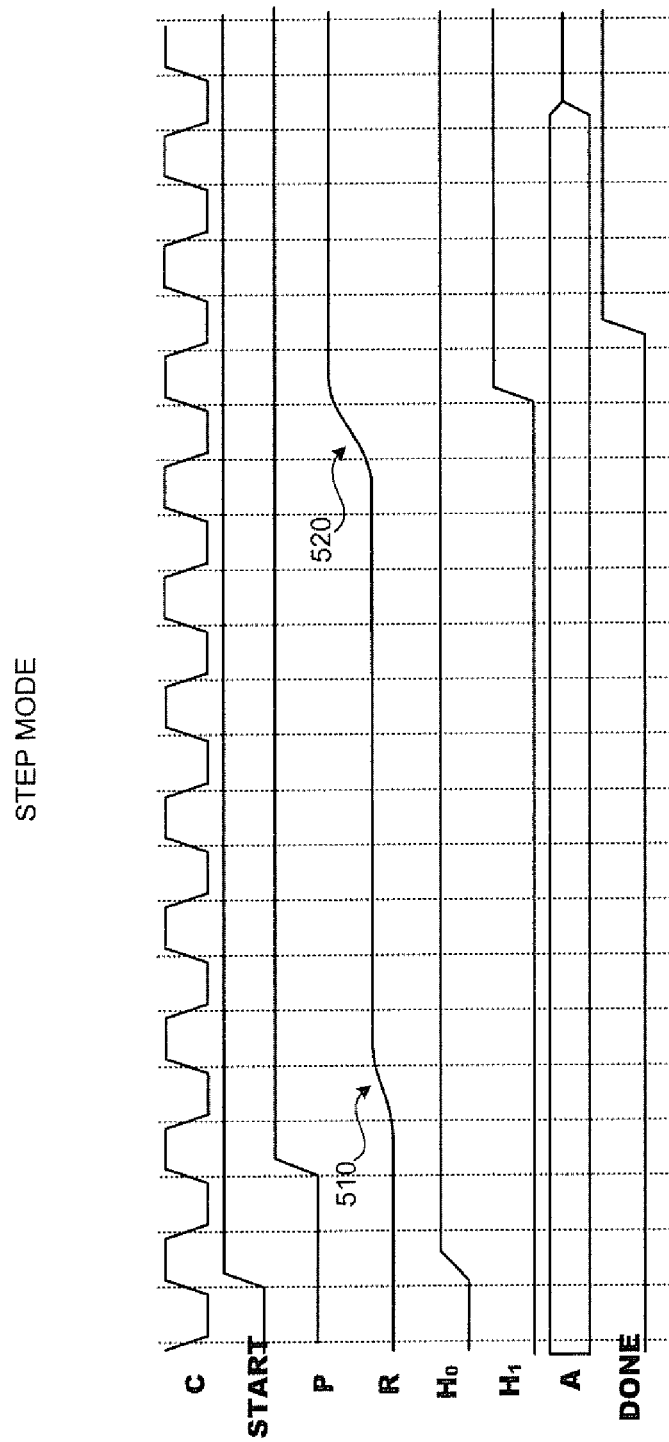
FIG. 5 is a timing diagram showing resulting signals of an exemplary step mode measurement.

In addition to normal vs. difference OTDR mode measurements, the exemplary system can also be configured to create pulse measurement or step measurements. For a pulse measurement, a short pulse (e.g., flash) of light is sent into the fiber 101 and then the reflected pulse is measured at discrete points by adjusting the values of H0 and H1. In the step mode, the light is turned on (e.g., steady) and the reflected light is measured as a function of time while the light remains on. FIGS. 4a and 4b show examples of pulse mode operation. FIG. 5 shows an example of step mode operation. In step mode operation, the signal P steps upwards and remains high for the duration of each OTDR measurement. As the light reflects from various discontinuities within the fiber 101, the signal R increases as each reflection is detected. This is evident in the profile changes 510 and 520 in R.

Figure 6:
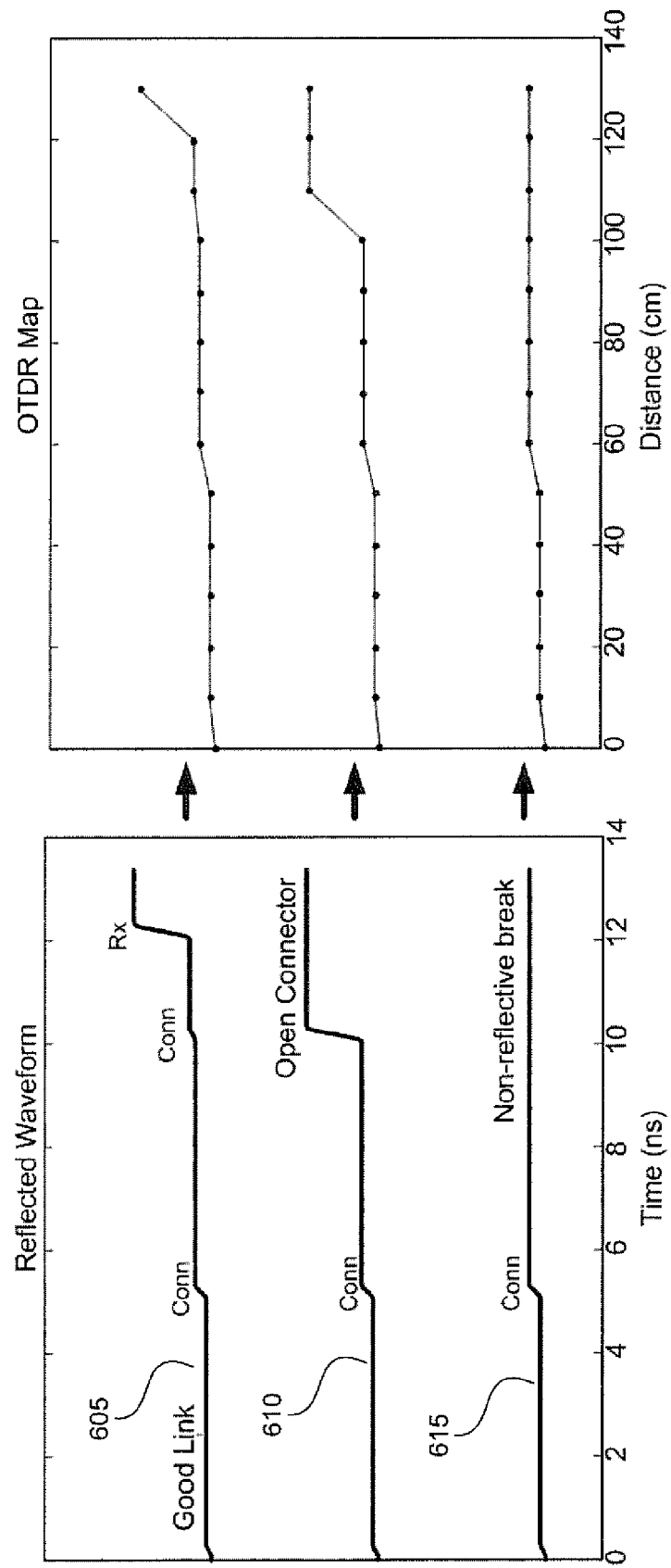
FIG. 6 is a timing diagram illustrating examples of a reflected signal and resulting OTDR mapping.

FIG. 6 illustrates examples of the reflected light waveforms for three different situations in step mode operation. The top line 605 illustrates the reflected waveform for a good link. Fiber connectors (Conn) may create small reflections, and the receiver (Rx) on the far end of the fiber typically produces a slightly larger reflection.

The middle line 610 illustrates the reflected waveform for an open connector or a reflective break at the location of the second connector (Open Connector). An open connector or reflective break creates a relatively larger reflection than a properly seated connector.

The bottom line 615 illustrates the reflected waveform for a non-reflective break. In this case, the break produces no reflection. These "reflections" can be mapped to their respective distances as shown in the accompanying OTDR Map.

One of several advantages of the step measurement mode is that a coarse set of measurements can be made to search for the step in reflected light, as opposed to the pulse mode where measurements must be made at a resolution fine enough to catch the reflected pulse, which is approximately half the pulse width. Because coarser time steps can be measured, the total number of measurements required may be less for the step measurement mode. Therefore, the step measurement mode may enable faster measurements.

Figure 7:
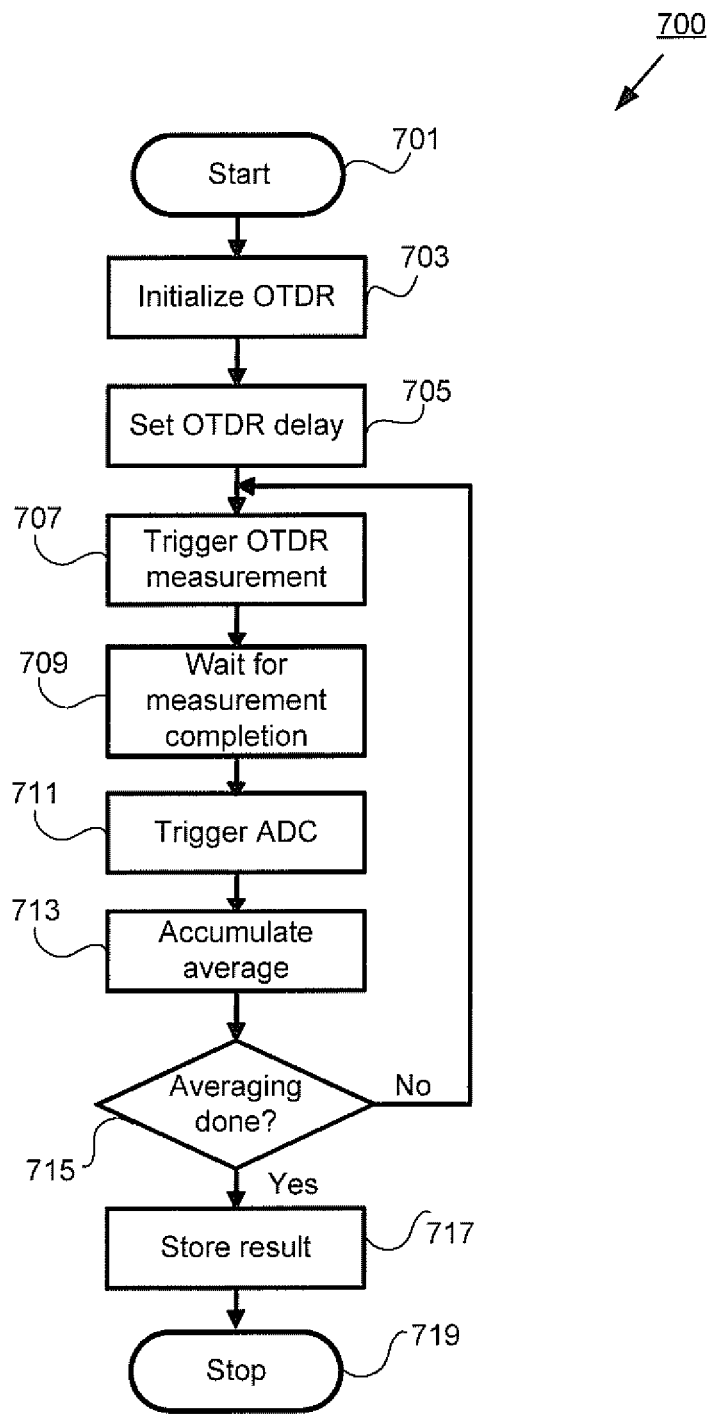
FIG. 7 is an exemplary flowchart of a microcontroller programming sequence to perform OTDR measurements.

FIG. 7 is an exemplary measurement flow process 700 diagram for a simple Go/No-Go measurement. Upon start of the measurement 701, the OTDR is initialized 703 which sets a particular OTDR delay 705, by setting the values of H0 and H1. Next, a set of measurements is triggered 707 at that set delay to enable averaging of the signal received, to improve signal accuracy. After measurement is completed 709, the ADCs are triggered 711 for sampling the measured value. The sampled measured value is accumulated to form an average 713. If additional values are needed 715, the process 700 returns to 707 to trigger another OTDR measurement. Alternatively, if additional values are not needed 715, then the process 700 proceeds to store the result 717, and proceed onto termination 719.

Within various steps or modules outlined above, a system processor can operate to perform averaging and comparison of the results to acceptable values (i.e., a "control" measurement). If the measured result is not within the acceptable values, the processor can execute a failure alert. For example, the system can alert operators of the problem, as one of many possible examples. Or a detailed mapping of the failing optical fiber can be initiated to isolate the failure.

Figure 8:
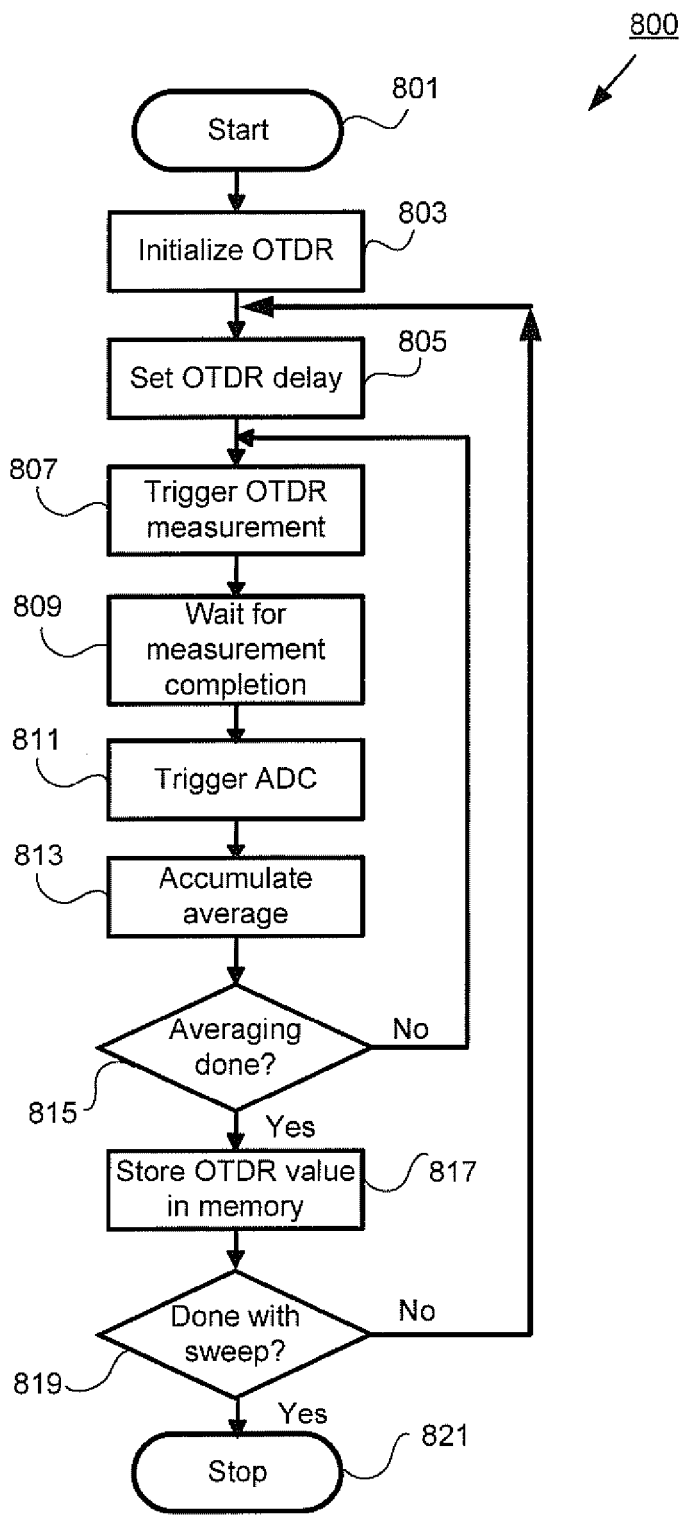
FIG. 8 is another exemplary flowchart of a microcontroller programming sequence to perform OTDR measurements.

FIG. 8 is another possible exemplary measurement flow process 800 diagram. In this example, the initial steps 801, 803, 805, 807, 809, 811, 813, 815, and 817 correspond to the same steps 701, 703, 705, 707, 709, 711, 713, 715, and 717 if FIG. 7. However, instead of terminating after the average for a given delay is calculated and stored in flash memory 817, the process 800 performs determines if all sweeps are completed 819 and if not, returns to step 805 and sets or increments another delay. Using this "new" delay, the signal at the next delay is measured. When the sequence of measurements is complete (sweep complete 819 is yes), the process 800 terminates 821 with data in memory that can "map" or "fingerprint" the reflected power vs. time profile for the optical fiber under test.

As an illustrative example of the above process(es) in operation, a 10 meter optical fiber system could be tested with a 10 cm resolution, requiring 100 measurements. If averaging of 1000 samples is used, then a total of 100,000 measurements must be made. If an external ADC is used, the setup and conversion time of the ADC dominates the measurement time and may be approximately 10 microseconds. Therefore the total measurement time would be approximately 1 second. If a fine diagnostic measurement with 1 cm resolution is desired, then the measurement would take 10 seconds. If faster measurement times were required, an ADC could be built into the integrated OTDR chip, reducing measurement time by approximately 10×. Other fast averaging methods could be implemented on-chip, such as analog averaging with discrete-time switch capacitors accumulating charge or a delta-sigma data converter Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor or microprocessor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

What is claimed is:

1. An apparatus capable of either high speed data transmission or optical time domain reflectometer (OTDR) measurement, comprising:
    an electrical multiplexer having a first coupled input for a data communications signal from an external source and a second coupled input for an OTDR signal, wherein the electrical multiplexer selects a signal from either the first or second coupled inputs for conversion into the optical domain;
    OTDR circuitry generating the OTDR signal;
    a processor controlling the OTDR circuitry;
    a light transmitter system coupled to an output of the electrical multiplexer;
    a light detector coupled to the OTDR circuitry; and
    a bi-directional optical coupling structure in a light path of the light transmitter system adapted for channeling a light to an input of the fiber optic line, and for channeling reflected light from the fiber optic line to the light detector;
    wherein at the generated OTDR signal is at least one of a pulse mode and a step mode is forwarded from the electrical multiplexer to the light transmitter system and input into the bi-directional optical coupling structure and into the fiber optic line, wherein a time delay in the reflected light is used to determine the distance of the disruption in the fiber optic line.

2. The apparatus of claim 1, further comprising a partially reflecting surface between the bi-directional optical coupling structure and the fiber optic line.

3. The apparatus of claim 1, further comprising a mirror to direct the reflected light to the light detector.

4. The apparatus of claim 1, further comprising a transparent substrate coupled on one side to the light transmitter system and light detector, and coupled on an opposite side to the bi-directional optical coupling structure.

5. The apparatus of claim 1, wherein the bi-directional optical coupling structure has at least one of a light splitting surface and a lens.

6. The apparatus of claim 1, further comprising an input clock signal and input start signal to the ODTR circuitry, to initiate an OTDR measurement sequence.

7. The apparatus of claim 1, further comprising an amplifier coupled to an output of the light detector.

8. The apparatus of claim 7, further comprising a track and hold circuit coupled to an output of the amplifier.

9. The apparatus of claim 8, wherein an output of the ODTR circuitry is input into the track and hold circuit.

10. The apparatus of claim 8, further comprising another amplifier coupled to an output of the track and hold circuitry.

11. The apparatus of claim 1, wherein the light transmitting system includes a vertical cavity surface emitting laser.

12. A method for performing optical time domain reflectometery with a data communications line in a signal path to a fiber optic line, comprising:
    configuring an electrical multiplexer to discontinue data transmission for conversion into the optical domain from a data communications source and enable OTDR signal transmission;
    generating an OTDR signal from OTDR circuitry coupled to the electrical multiplexer with a data signal input also coupled to the electrical multiplexer;
    operating the OTDR signal in at least one of a pulse mode and step mode;
    driving a light transmitter system that is coupled to an output of the electrical multiplexer based on the OTDR signal;
    forwarding light from the light transmitter system to the fiber optic line via a bi-directional optical coupling structure;
    channeling reflected light from the fiber optic line via the bi-directional optical coupling structure to a light detector;

measuring the reflected light time delay as compared to a start time of the OTDR signal;

averaging measured delays to obtain an average; and calculating a distance of a disruption in the fiber optic line based on the obtained average.

13. The method of claim 12, wherein the pulse mode is operated in at least one of a calibration mode and difference mode, wherein the calibration mode utilizes a reflection from a known reference surface.

14. The method of claim 12, further comprising sending at least two reference signals from the ODTR circuitry to a track and hold device.

15. The method of claim 14, further comprising:

applying a differential variable gain to an output of the track and hold device; and digitizing an output of the differential variable gain, wherein the calculated distance is determined by a processor operating on information from the digitized output.

16. The method of claim 12, further comprising generating an OTDR distance map.

17. The method of claim 12, further comprising:

sending a start signal to the ODTR circuitry;

triggering ODTR measurement based on determined triggering delays;

waiting for ODTR measurement completion;

triggering an analog-to-digital conversion of measured information;

accumulating an average of the measured information; and storing the average as the obtained average.

18. The method of claim 17, further comprising:

obtaining a secondary obtained average based on a plurality of sets of determined triggering delays; and calculating the distance of a disruption in the fiber optic line based on the obtained average being derived from the plurality of sets of determined triggering delays.

19. The method of claim 18, wherein the plurality of sets of determined triggering delays is based on a completion of sweep determination.

20. An apparatus capable of either high speed data transmission or optical time domain reflectometer (OTDR) measurement, comprising:

means for multiplexing a first coupled input for a data communications signal from an external source and a second coupled input for an OTDR signal, wherein the multiplexer means selects a signal from either the first or second coupled inputs for conversion into the optical domain;

means for generating the OTDR signal;

means for controlling the means for generating;

means for generating light, coupled to an output of the means for multiplexing;

means for detecting light coupled to the means for generating; and means for bi-directionally coupling light from the means for generating light to an input of the fiber optic line, and for channeling reflected light from the fiber optic line to the means for detecting light, wherein the generated OTDR signal is at least one of a pulse mode and step mode and wherein a time delay in the reflected light is used to determine a distance of the disruption in the fiber optic line.

21. The apparatus of claim 1, wherein at least one of the electrical multiplexer, light transmitter system, and the OTDR circuitry is contained within a single integrated circuit.

22. The apparatus of claim 1, where the light transmitting system is capable of transmitting optical data at least 2 billion bits per second.

23. The apparatus of claim 21, where a package height of the component is less than 5 mm.

24. The apparatus of claim 1, where a resolution of the OTDR measurement is less than 10 cm.

* * * * *